(12) United States Patent
Weisend et al.

(10) Patent No.: US 10,369,351 B2
(45) Date of Patent: Aug. 6, 2019

(54) ELECTRODE INTERFACES AND ELECTRODE ASSEMBLIES FOR PERFORMING TRANSCRANIAL DIRECT CURRENT STIMULATION

(71) Applicants: Michael P. Weisend, Yellow Springs, OH (US); Matthew S. Sherwood, Sidney, OH (US); Megan K. Howes, Venice, FL (US)

(72) Inventors: Michael P. Weisend, Yellow Springs, OH (US); Matthew S. Sherwood, Sidney, OH (US); Megan K. Howes, Venice, FL (US)

(73) Assignee: Wright State University, Dayton, OH (US)

( * ) Notice: Subject to any disclaimer, the term of this patent is extended or adjusted under 35 U.S.C. 154(b) by 106 days.

(21) Appl. No.: 15/784,697

(22) Filed: Oct. 16, 2017

(65) Prior Publication Data

US 2018/0126150 A1    May 10, 2018

Related U.S. Application Data

(60) Provisional application No. 62/408,636, filed on Oct. 14, 2016.

(51) Int. Cl.
| | | |
|---|---|---|
| *A61N 1/00* | (2006.01) | |
| *A61N 1/04* | (2006.01) | |
| *A61N 1/20* | (2006.01) | |
| *A61N 1/36* | (2006.01) | |

(52) U.S. Cl.
CPC ......... *A61N 1/0456* (2013.01); *A61N 1/0476* (2013.01); *A61N 1/20* (2013.01); *A61N 1/36025* (2013.01)

(58) Field of Classification Search
CPC .. A61N 1/0456; A61N 1/0476; A61N 1/0472; A61N 1/36025; A61N 1/20
See application file for complete search history.

(56) References Cited

U.S. PATENT DOCUMENTS

| | | |
|---|---|---|
| 4,265,253 A | 5/1981 | Abraham |
| 5,330,527 A | 7/1994 | Montecalvo et al. |
| 8,688,239 B2 | 4/2014 | Hartlep et al. |
| 2007/0213796 A1 | 9/2007 | McGinnis |
| 2013/0268038 A1 | 10/2013 | Bikson et al. |
| 2016/0206871 A1 | 7/2016 | Weisend |

*Primary Examiner* — Scott M. Getzow
(74) *Attorney, Agent, or Firm* — Dinsmore & Shohl LLP

(57) ABSTRACT

Electrode interfaces and electrode assemblies for performing transcranial direct current stimulation. The electrode interfaces include a body configured to be coupled to an electrode for delivery of electrical current therethrough. The body includes a non-contact surface and a contact surface opposing the non-contact surface. The body defines a plurality of conductivity passages extending therethrough from the non-contact surface to the contact surface. Each conductivity passage is disposed along a central axis and includes at least one branching inlet and at least one branching subpassage extending from the at least one branching inlet to the contact surface. Each branching subpassage defines a plurality of branches, and each branch diverges from the central axis and then extends to the contact surface. The electrode assemblies include a neurostimulation device, at least two electrodes coupled to the neurostimulation device, and an electrode interface including a body coupled to each electrode.

15 Claims, 18 Drawing Sheets

ELECTRODE INTERFACES AND ELECTRODE ASSEMBLIES FOR PERFORMING TRANSCRANIAL DIRECT CURRENT STIMULATION

CROSS-REFERENCE TO RELATED APPLICATIONS

This application claims the benefit under 35 U.S.C. § 119 of U.S. Provisional Patent Application No. 62/408,636, filed on Oct. 14, 2016, entitled, "Transdermal Electrical Stimulation Electrodes with Distributed Current Densities", the contents of which are hereby incorporated by reference in their entirety.

STATEMENT OF GOVERNMENT RIGHTS

This invention was made with government support under Grant No. FA8650-11-C-6157 awarded by the Air Force Research Lab. The Government has certain rights in this invention.

TECHNICAL FIELD

The present disclosure relates generally to electrode interfaces and to electrode assemblies, and more particularly, to electrode interfaces and electrode assemblies for performing transcranial direct current stimulation.

BACKGROUND

Transcranial direct current electrical stimulation (i.e., tDCS) is a form of neurostimulation that delivers constant, low direct current to the scalp of a subject for therapeutic purposes via the use of electrodes. Delivery of such current may affect neuronal excitability in a stimulated region. Unfortunately, many electrodes used in tDCS produce substantial localized current densities, such as, e.g., at the outer edges of the electrodes and/or at the interface of the electrodes and the subject undergoing tDCS. Such localized current densities may be painful and/or uncomfortable to the subject receiving the current. Thus, additional embodiments for tDCS electrodes with lower localized current densities at the outer edges thereof are desired.

SUMMARY

In embodiments, electrode interfaces are disclosed. The electrode interfaces include a body configured to be coupled to an electrode for delivery of electrical current therethrough. The body includes a non-contact surface and a contact surface opposing the non-contact surface, wherein the body defines a plurality of conductivity passages extending therethrough from the non-contact surface to the contact surface. Each conductivity passage is disposed along a central axis and includes at least one branching inlet, and at least one branching subpassage extending from the at least one branching inlet to the contact surface. Each branching subpassage defines a plurality of branches, and each branch diverges from the central axis and then extends to the contact surface.

In other embodiments, electrode assemblies for performing transcranial direct current stimulation are disclosed. The electrode assemblies include a neurostimulation device, at least two electrodes coupled to the neurostimulation device, and an electrode interface including a body coupled to each electrode for delivery of electrical current therethrough. The body includes a non-contact surface and a contact surface opposing the non-contact surface, wherein the body defines a plurality of conductivity passages extending therethrough from the non-contact surface to the contact surface. Each conductivity passage is disposed along a central axis and includes at least one branching inlet, and at least one branching subpassage extending from the at least one branching inlet to the contact surface. Each branching subpassage defines a plurality of branches, and each branch diverges from the central axis and then extends to the contact surface.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The following detailed description of the embodiments of the present disclosure can best understood when read in conjunction with the following drawings, where like structure is indicated with like reference numerals, in which:

FIG. 5 is perspective view of a transcranial direct current electrode assembly coupled to a subject.

DETAILED DESCRIPTION

Figure 1:
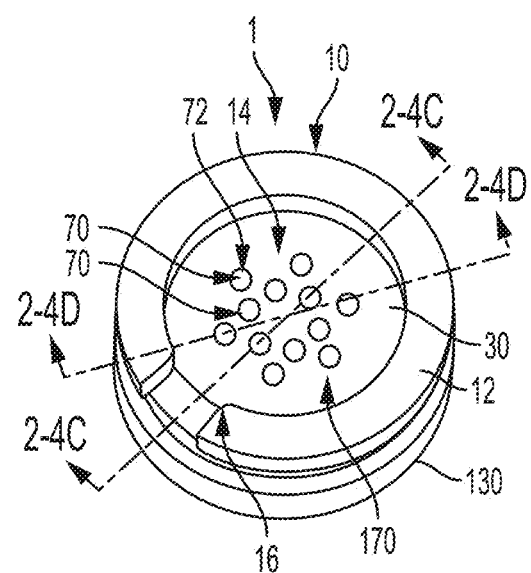
FIG. 1 is an upper perspective view of an electrode interface according to embodiments of the present disclosure.

Embodiments of the present disclosure relate to electrode interfaces and to electrode assemblies for performing transcranial direct current stimulation. Embodiments of electrode interfaces will now be described in detail with reference to FIGS. 1-3D and 4A-5. Thereafter, embodiments of electrode assemblies for performing transcranial direct current stimulation will be described in detail with reference to FIGS. 1 and 5.

I. Electrode Interfaces

Electrode interfaces are disclosed. In embodiments, the electrode interfaces include a body configured to be coupled to an electrode for delivery of electrical current therethrough. The body includes a non-contact surface and a contact surface opposing the non-contact surface, wherein the body defines a plurality of conductivity passages extending therethrough from the non-contact surface to the contact surface. Each conductivity passage is disposed along a central axis and includes at least one branching inlet and at least one branching subpassage extending from the at least one branching inlet to the contact surface, wherein each branching subpassage defines a plurality of branches, and wherein each branch diverges from the central axis and then extends to the contact surface.

Referring to FIGS. 1, 2A, 3A, and 4A, embodiments of the body 10 of the electrode interface 1 are depicted. In embodiments, the body 10 includes a non-contact surface 30, a contact surface 50, a side surface 130, and an inner surface 150. In some embodiments, the non-contact surface 30 and the contact surface 50 are opposing surfaces. In some embodiments, the non-contact surface 30 and the contact surface 50 are parallel. In some embodiments, the non-contact surface 30 and/or the contact surface 50 are planar.

In embodiments, the body 10 includes a rim region 12. In some embodiments, the rim region 12 is provided along an outer edge, such as, e.g., a circumference, of the body 10. In some embodiments, the rim region 12 is provided along a portion of an outer edge of the non-contact surface 30 of the body 10. In some embodiments, the rim region 12 is provided along 50% to 95%, or 60% to 90%, or 70% to 80%, or 75% of an outer edge, such as, e.g., a circumference, of the non-contact surface 30. In this way, the rim region 12 includes a cut-out 16.

In embodiments, the body 10 includes a recessed region 14. In some embodiments, the recessed region 14 is provided in an inner region 170 of the body 10. In some embodiments, the recessed region 14 is defined by the rim region 12 and the non-contact surface 30. In some embodiments, the body 10 includes a circular, ovular, rectangular, square, or irregular shape. In some embodiments, the body 10 includes a circular shape.

Figure 5:
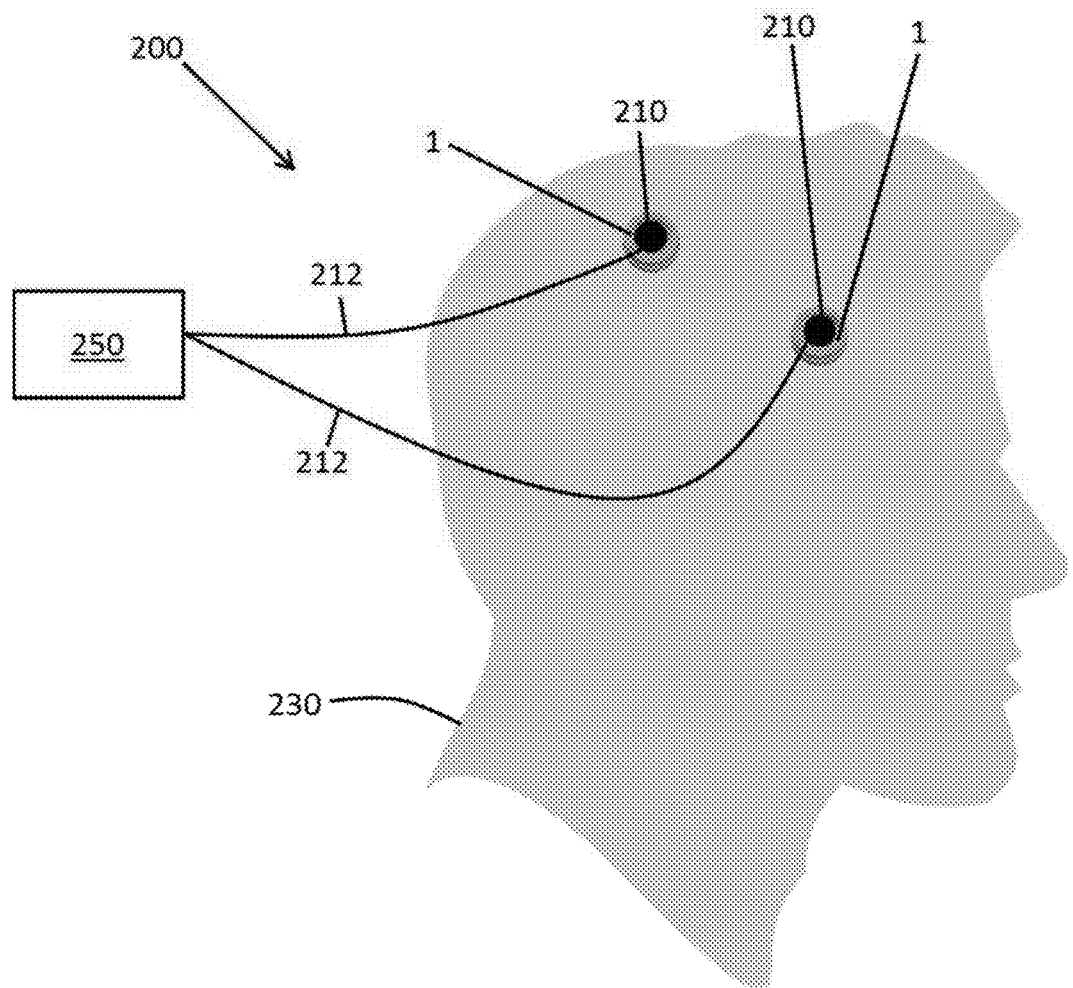
FIG. 5 is a perspective view of an electrode assembly including the electrode interface of FIG. 1 coupled to a subject; more specifically.

Referencing FIGS. 1 and 5, in embodiments, the body 10 is configured to be coupled to an electrode 210 for delivery of electrical current therethough. The body 10 may be shaped and/or sized to accommodate an electrode 210 (which will be described in greater detail in a later section). In some embodiments, the body 10 is shaped and/or sized to accommodate an electrode 210 such that the electrode 210 contacts a portion thereof and is capable of delivering electrical current therethrough. The electrode 210 may be placed and/or disposed within the recessed region 14 such that it directly or indirectly contacts the body 10 and/or the at least one conductivity passage 70 thereof and is capable of delivering electrical current therethrough. For example, in some embodiments wherein the body 10 includes a recessed region 14, the recessed region 14 may be sized and/or shaped to accommodate an electrode 210. In this way, an electrode 210 may be placed and/or disposed within the recessed region 14 such that it directly contacts the non-contact surface 30 and/or at least one conductivity passage 70.

Referencing FIGS. 1, 2A, 3A, and 4A, in embodiments, the body 10 defines a plurality of conductivity passages 70 therethrough. In some embodiments, the inner surface 150 of the body 10 defines the conductivity passages 70 therethrough. As used herein, the term "therethrough" refers to the extension of a passage, such as, e.g., a conductivity passage 70, through a structure. In some embodiments, the conductivity passages 70 extend through the body 10 from the non-contact surface 30 to the contact surface 50. In this way, each conductivity passage 70 includes openings on both the non-contact surface 30 and the contact surface 50 of the body 10. In some embodiments, each conductivity passage 70 independently includes, without limitation, a circular, ovular, rectangular, square, or irregular cross-sectional shape. In some embodiments, each conductivity passage 70 includes a circular cross-sectional shape. In embodiments wherein a conductivity passage 70 includes a circular cross-sectional shape, the conductivity passage 70 may include a diameter of from 0.001 mm to 2 mm, of from 0.005 mm to 1.5 mm, of from 0.008 mm to 1 mm, of from 0.009 mm to 0.5 mm, or of from 0.01 mm to 0.2 mm. In some embodiments, a conductivity passage 70 having a circular cross-sectional shape includes a uniform, tapered, and/or non-uniform diameter.

Referring to FIGS. 1, 2C, 3C, and 4C, in embodiments, the body 10 defines a conductivity inlet 72 and a conductivity outlet 74 for each the conductivity passages 70 extending therethrough. In some embodiments, the conductivity inlet 72 is defined by the non-contact surface 30. In some embodiments, the conductivity outlet 74 is defined by the contact surface 50. In some embodiments, each conductivity passage 70 extends from a conductivity inlet 72 to a conductivity outlet 74.

In embodiments, each conductivity passage 70 independently extends through the body 10 at a length of from 0.5 mm to 5 mm, or from 0.6 mm to 4.5 mm, or from 0.7 mm to 4 mm, or from 0.8 mm to 3.5 mm, or from 0.9 mm to 3 mm, or from 1 mm to 2.5 mm, or from 1.1 mm to 2.4 mm, or from 1.2 mm to 2.2 mm, or from 1.3 mm to 1.9 mm, or from 1.5 mm to 1.8 mm, or from 1.6 mm to 1.7 mm. In some embodiments, each conductivity passage 70 independently extends through the body 10 at a length of at least 0.5 mm, or at least 0.6 mm, or at least 0.7 mm, or at least 0.8 mm, or at least 0.9 mm, or at least 1 mm, or at least 1.1 mm, or at least 1.2 mm, or at least 1.3 mm, or at least 1.4 mm, or at least 1.5 mm, or at least 1.6 mm, or at least 1.7 mm, or at least 1.8 mm, or at least 1.9 mm, or at least 2 mm, or at least 2.2 mm, or at least 2.4 mm, or at least 2.5 mm, or at least 3 mm, or at least 3.5 mm, or at least 4 mm, or at least 4.5 mm, or at least 5 mm.

In embodiments, the body 10 defines at least two, or at least three, or at least six, or at least eight, or at least ten, or at least twelve conductivity passages 70 extending therethrough. In some embodiments, the body 10 defines twelve conductivity passages 70 extending therethrough. Referring to FIG. 1, in embodiments wherein the body 10 defines at least six conductivity passages 70 extending therethrough, the conductivity passages 70 and/or conductivity inlets 72 thereof may be arranged in a triangle configuration, a hexagon configuration, and/or a hexagram configuration. In some embodiments, the body 10 defines the conductivity passages 70 in the inner region 170 and/or the recessed region 14 of the body 10. In some embodiments, the body 10 defines the conductivity passages 70 in a central, inner region 170 of the recessed region 14 of the body 10.

Referencing FIGS. 2C-2D, 3C-3D, and 4C-4D, in embodiments, each conductivity passage 70 is independently disposed along a central axis 110. In embodiments, each conductivity passage 70 is independently disposed along a central axis 110 and extends in a vertical direction. In some embodiments, each conductivity passage 70 is tubular. In some embodiments, each conductivity passage 70 includes at least one branching inlet 76 and at least one branching subpassage 90 extending from the branching inlet 76. In some embodiments, each branching inlet 76 is defined by a conductivity passage 70 and/or the inner surface 150 of the body 10.

In embodiments, each branching subpassage 90 independently defines a plurality of branches 92. Each branch 92 may independently diverge from the central axis 110 of the respective conductivity passage 70 and then extend to the contact surface 50. In some embodiments, each branch 92 diverges from the central axis 110 in a first direction X away from the central axis 110. In some embodiments, each branch 92 diverges laterally from the central axis 110 in a first direction X. In some further embodiments, each branch 92 diverges laterally from the central axis 110 in a first direction X toward a side surface 130.

Figure 4A:
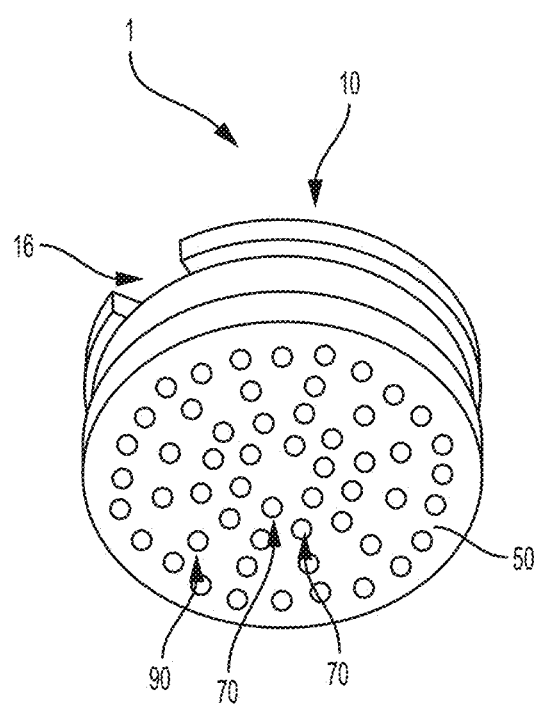
FIG. 4A is a bottom perspective view of the electrode interface of FIG. 1 according to embodiments of the present disclosure.
Figure 4B:
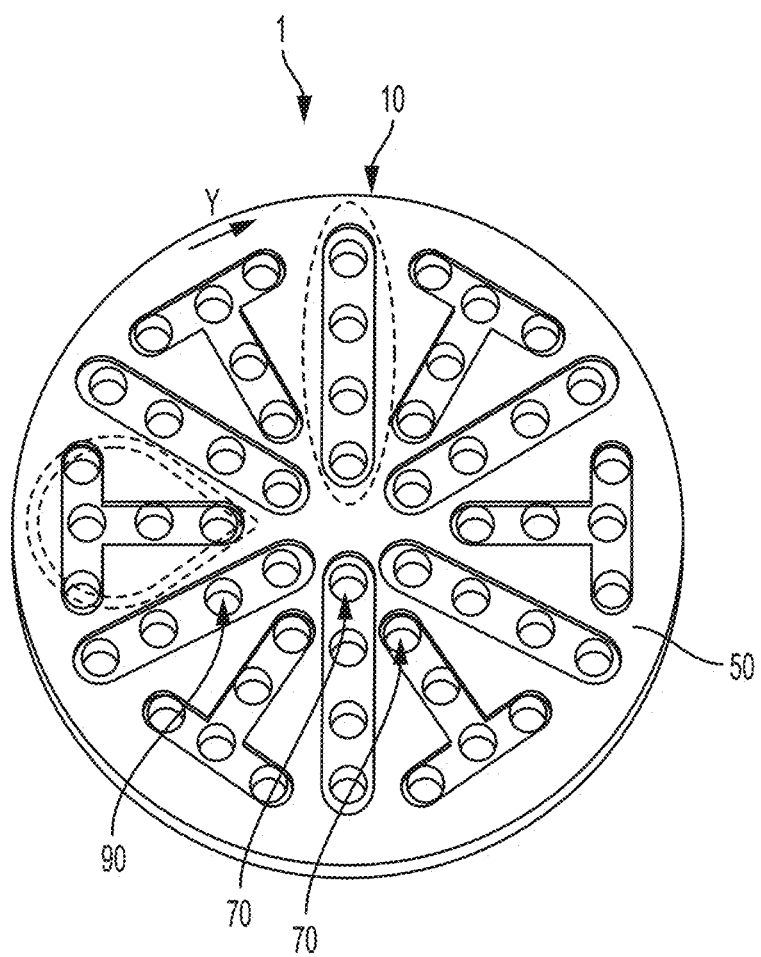
FIG. 4B is a bottom plan view of the electrode interface of FIG. 4A according to embodiments of the present disclosure.
Figure 4C:
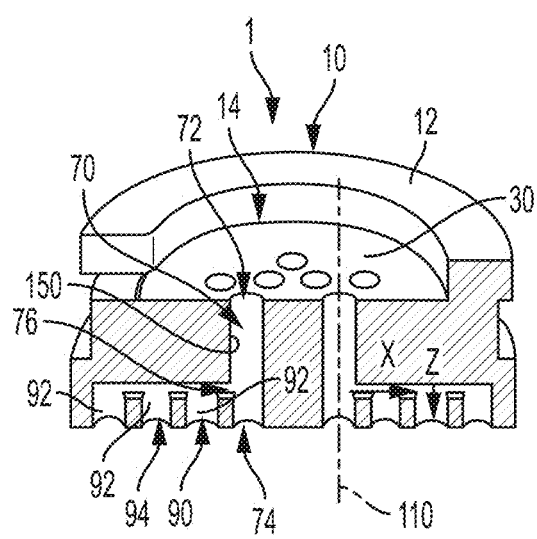
FIG. 4C is a section view of the electrode interface of FIG. 4A taken along section line 2-4C of FIG. 1 according to embodiments of the present disclosure.
Figure 4D:
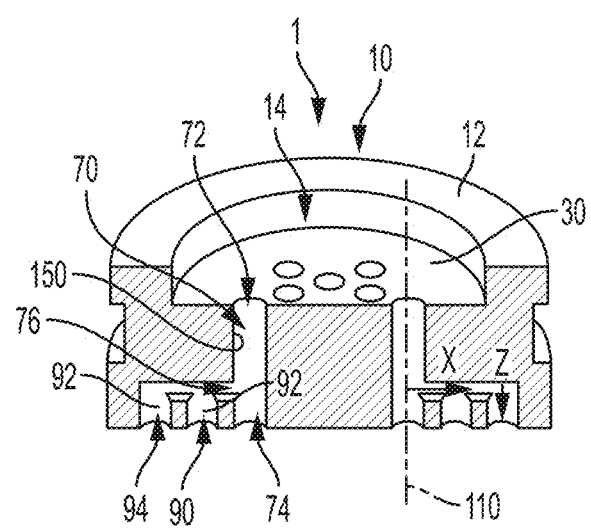
FIG. 4D is a section view of the electrode interface of FIG. 4A taken along section line 2-4D of FIG. 1 according to embodiments of the present disclosure.

Referring to FIG. 4B, in some embodiments, after diverging in a first direction X away from the central axis 110, each branch 92 optionally independently diverges from the central axis 110 in a second direction Y away from the first direction X. In some embodiments, each branch 92 diverges from the central axis 110 in a second direction Y which is normal to the first direction X. In embodiments, the second direction Y extends along the outer edge of the body 10.

Referring to FIGS. 2C-2D, 3C-3D, and 4C-4D, after diverging in the first direction X and (optionally) in the second direction Y, each branch 92 may independently extend in a second or third direction Z to the contact surface 50. In some embodiments, each branch 92 extends vertically to the contact surface 50 in a second or third direction Z which is normal to the first direction X and/or the second direction Y. In some embodiments, each branch 92 extends vertically to the contact surface 50 in a second or third direction Z which is parallel to the central axis 110. In this way, each branch 92 of a branching subpassage 90 includes an opening on the contact surface 50 of the body 10. In some embodiments, each branch 92 independently includes, without limitation, a circular, ovular, rectangular, square, or irregular cross-sectional shape. In some embodiments, each branch 92 independently includes a circular cross-sectional shape. In some embodiments wherein a branch 92 includes a circular cross-sectional shape, the branch 92 may include a diameter of from 0.001 mm to 2 mm, of from 0.005 mm to 1.5 mm, of from 0.008 mm to 1 mm, of from 0.009 mm to 0.5 mm, or of from 0.01 mm to 0.2 mm. In some embodiments, the branch 92 including a circular cross-sectional shape includes a uniform, tapered, and/or non-uniform diameter.

Referring to FIGS. 2A-2B, 3A-3B, and 4A-4B, in embodiments, the body 10 defines a branching outlet 94 for each branch 92. In some embodiments, each branching outlet 94 is defined by the contact surface 50. Referring to FIGS. 1, 2B, 3B, and 4B, in some embodiments, the body 10 defines from two to four times as many branching outlets 94 as conductivity inlets 72. In some embodiments, the body 10 defines from two to three times as many branching outlets 94 as conductivity inlets 72.

Figure 2A:
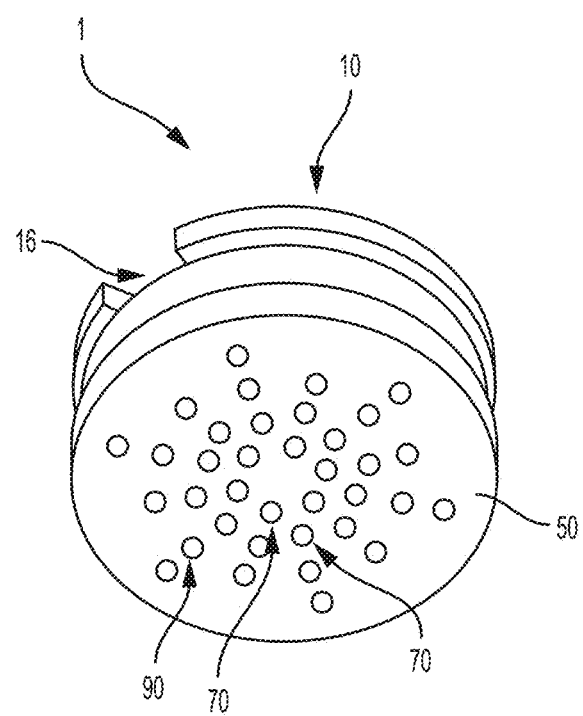
FIG. 2A is a bottom perspective view of the electrode interface of FIG. 1 according to embodiments of the present disclosure.
Figure 2B:
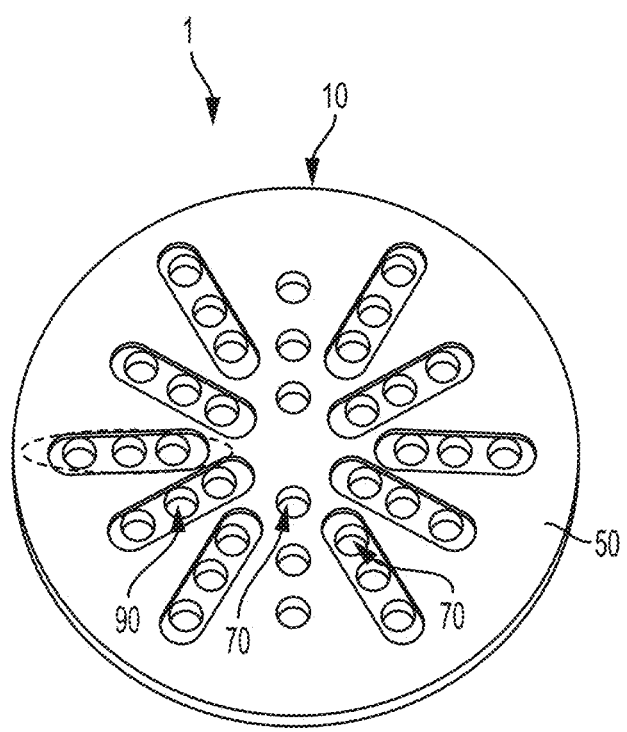
FIG. 2B is a bottom plan view of the electrode interface of FIG. 2A according to embodiments of the present disclosure.
Figure 2C:
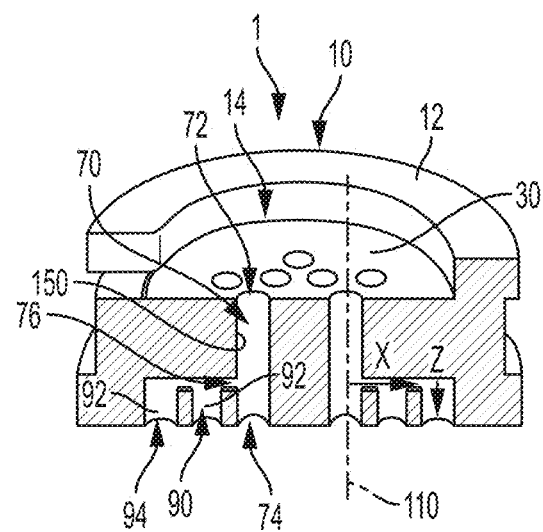
FIG. 2C is a section view of the electrode interface of FIG. 2A taken along section line 2-4C of FIG. 1 according to embodiments of the present disclosure.
Figure 2D:
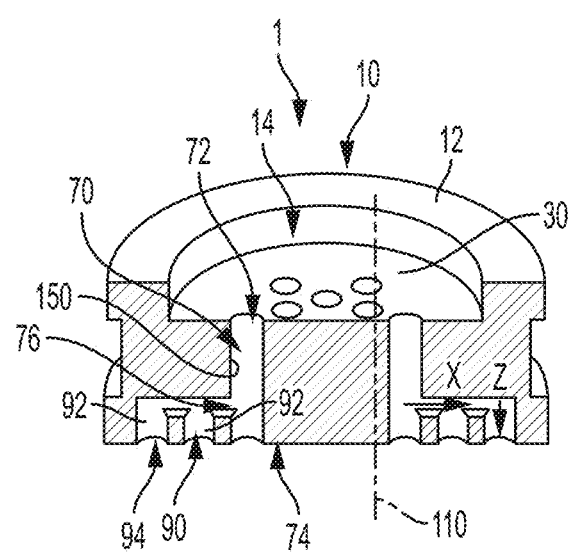
FIG. 2D is a section view of the electrode interface of FIG. 2A taken along section line 2-4D of FIG. 1 according to embodiments of the present disclosure.
Figure 3A:
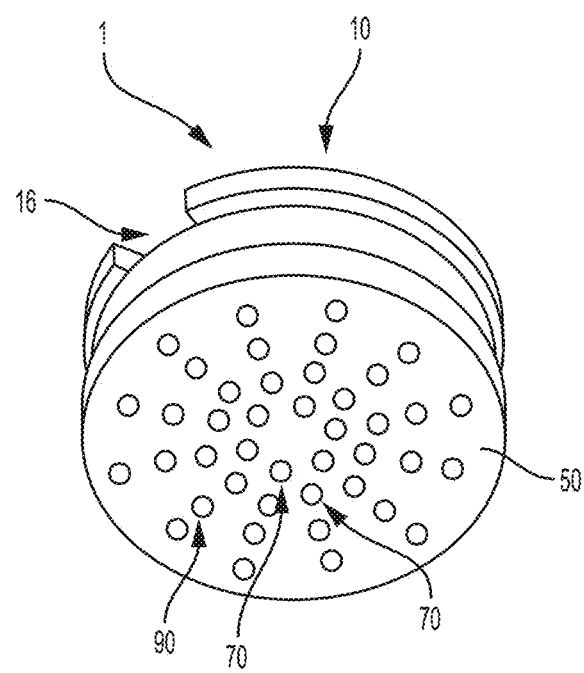
FIG. 3A is a bottom perspective view of the electrode interface of FIG. 1 according to embodiments of the present disclosure.
Figure 3B:
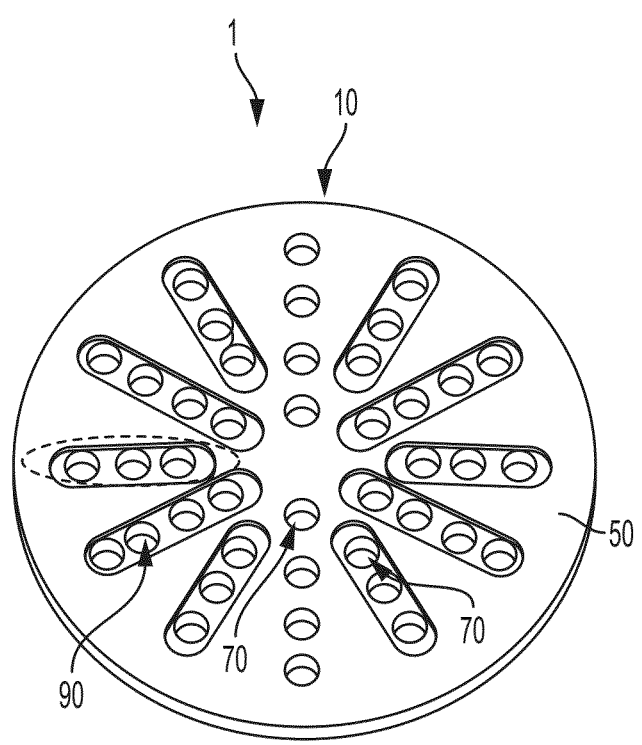
FIG. 3B is a bottom plan view of the electrode interface of FIG. 3A according to embodiments of the present disclosure.
Figure 3C:
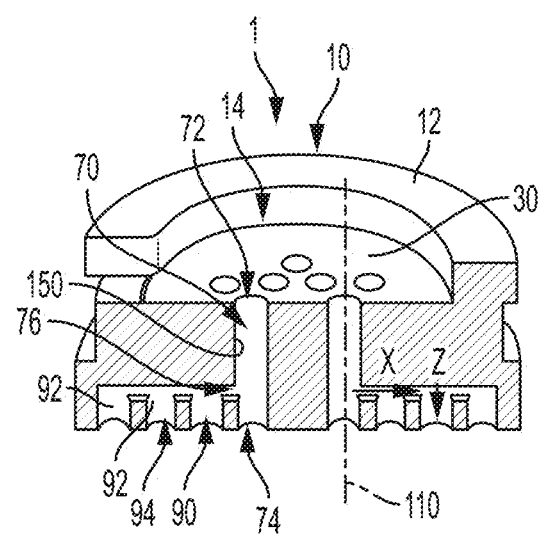
FIG. 3C is a section view of the electrode interface of FIG. 3A taken along section line 2-4C of FIG. 1 according to embodiments of the present disclosure.
Figure 3D:
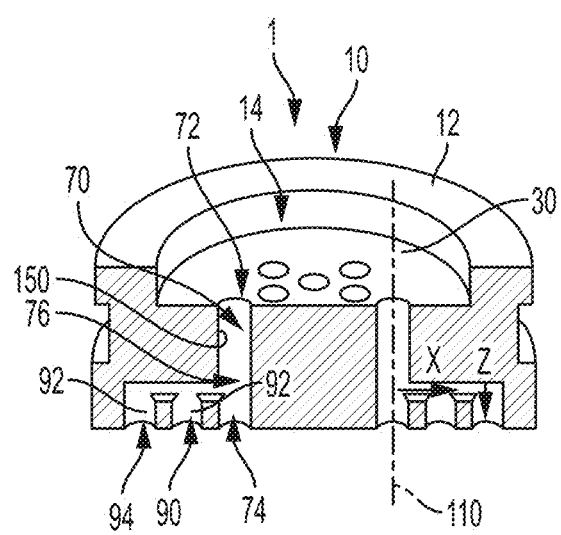
FIG. 3D is a section view of the electrode interface of FIG. 3A taken along section line 2-4D of FIG. 1 according to embodiments of the present disclosure.

Referring to FIGS. 2B, 3B, and 4B, in embodiments wherein each branching subpassage 90 includes a plurality of branching outlets 94, the conductivity outlet 74 of the conductivity passage 70 and/or the respective branching outlets 94 of the branching subpassage 90 thereof may be arranged in an inline or series configuration (indicated via dashed lines). Referring to FIG. 4B, in embodiments wherein each branching subpassage 90 includes a plurality of branching outlets 94, the conductivity outlet 74 of the conductivity passage 70 and/or the respective branching outlets 94 of the branching subpassage 90 thereof may be arranged in a cross configuration (indicated via double dashed lines). As used herein, the term "cross configuration" refers to two series of intersecting outlets, wherein one series of outlets is in a column and another series of outlets is in a row.

In embodiments, each branching subpassage 90 independently defines at least two or at least three branches 92 thereof. In some embodiments, each branching subpassage 90 independently defines two or three branches 92 thereof.

In embodiments, the body 10 is formed from a plastic and/or non-conductive material. In illustrative, non-limiting embodiments, the body 10 is formed from a plastic polymer material chosen from polyamides, polycarbonates, polyesters, polyethylenes, polypropylenes, polystyrenes, polyurethanes, polyvinyl chlorides, polyvinylidene chlorides, polylactic acids, polyvinyl alcohols, acrylonitrile butadiene styrenes, and combinations thereof. In some illustrative, non-limiting embodiments, the body 10 is formed from a plastic polymer material chosen from polyvinyl alcohols, polylactic acids, acrylonitrile butadiene styrenes, and combinations thereof. The body 10 may be formed via manufacturing methods known to those of ordinary skill in the art, including, e.g., 3D printing and/or various molding methods.

In some embodiments, the electrode interfaces 1 described herein are used for performing transcranial direct current stimulation, as described in greater detail in a later section.

Embodiments of electrode interfaces 1 have been described in detail. Embodiments of electrode assemblies for performing transcranial direct current stimulation will now be described in detail with reference to FIGS. 1 and 5.

II. Electrode Assemblies for Performing Transcranial Direct Current Stimulation

Electrode assemblies for performing transcranial direct current stimulation are disclosed. In embodiments, the electrode assemblies include a neurostimulation device, at least two electrodes 210 coupled to the neurostimulation device, and an electrode interface 1 including a body 10 coupled to each electrode 210 for delivery of electrical current therethrough. The body 10 includes a non-contact surface 30 and a contact surface 50 opposing the non-contact surface 30, wherein the body 10 defines a plurality of conductivity passages 70 extending therethrough from the non-contact surface 30 to the contact surface 50. Each conductivity passage 70 is disposed along a central axis 110 and includes at least one branching inlet 94 and at least one branching subpassage 90 extending from the at least one branching inlet 94 to the contact surface 50. Each branching subpassage 90 defines a plurality of branches 92, and each branch 92 diverges from the central axis 110 and then extends to the contact surface 50.

Referencing FIG. 5, embodiments of electrode assemblies 200 for performing transcranial direct current stimulation are depicted. In embodiments, the electrode assemblies 200 include a neurostimulation device 250, at least two electrodes 210 coupled to the neurostimulation device 250, and an electrode interface 1 coupled to each electrode 210 for delivery of electrical current therethrough. In some embodiments, the neurostimulation device 250 delivers constant, low direct current to the scalp of a subject 230. In illustrative, non-limiting embodiments, the neurostimulation device 250 may be a stimulator which includes multiple independent and isolated channels with a common reference channel. Examples of a suitable neurostimulation device 250 include, but should not be limited to, an M×N HD-tDCS stimulator and a M×N HD-tES stimulator, available from Soterix Medical Inc. (New York, N.Y.).

Still referencing FIG. 5, in embodiments, at least two electrodes 210 are coupled to the neurostimulation device 250. In embodiments, the electrodes 210 are independently chosen from ring and disc electrodes. In some embodiments, the electrodes 210 are independently chosen from silver/silver chloride ring and/or disc electrodes. However, any electrodes 210 may be used which are capable of delivering electrical current through the electrode interface 1, such as, e.g., through a conductive contact medium disposed therein. In some embodiments, the electrodes 210 include a cathode electrode and an anode electrode.

In embodiments, the electrodes 210 are coupled to the neurostimulation device 250. In some embodiments, the 210 are electrically coupled to the neurostimulation device 250 through wires and/or cables 212 such that electrical signals and/or electrical current may be exchanged therebetween. In embodiments, at least a portion of the wires and/or cables 212 are accommodated by the cut-out 16 of the rim region 12 of the body 10. In some embodiments, at least a portion of the wires and/or cables 212 are placed and/or disposed within the cut-out 16 such that they directly or indirectly contact the body 10.

In embodiments, the electrode assemblies 200 include an electrode interface 1. The electrode interface 1 includes a body 10 coupled to each electrode 210 for delivery of electrical current, e.g., direct current, therethrough. The electrode interface 1 is as described in a previous section. Additionally, as also described in a previous section, each body 10 may be shaped and/or sized to accommodate each electrode 210.

In embodiments, the electrode assemblies 200 include a conductive contact medium disposed within the plurality of conductivity passages 70 and/or the at least one branching subpassage 90 of the body 10. In some embodiments, the conductive contact medium is chosen from saline, a conductive gel, and/or a conductive cream. In some embodiments, the conductive contact medium is an electrode gel chosen from saline, a conductive gel, and/or a conductive cream. In some embodiments, the conductive contact medium has a conductivity of less than 4 S/m, or of less than 3 S/m, or of less than 2 S/m. In some embodiments, the conductive contact medium has a conductivity of from 0.1 S/m to 2 S/m.

In use, such as, e.g., in performing transcranial direct current stimulation, the contact surface 50 of each electrode interface 1 coupled to each electrode 210 is independently provided to a region of interest on a subject 230. In some embodiments, the contact surface 50 of each electrode interface 1 is independently placed in a region of interest on a subject's scalp. In some embodiments, the electrode interface 1 includes a conductive contact medium disposed within the conductivity passages 70 and/or the branching subpassages 90 thereof. In this way, the contact surface 50 and/or the conductive contact medium disposed within the conductivity passages 70 and/or the branching subpassages 90 thereof (and exiting through the conductivity outlets 74 and/or branching outlets 94) may directly contact the subject 230, such as, e.g., via the subject's scalp.

Then, in use, a constant, low direct current is delivered to the electrode through the conductive contact medium of the electrode interface 1 to stimulate a target region of the subject 230. In embodiments, current delivered to the subject 230 is from 1 mA to 2 mA, or from 1.1 mA to 1.9 mA, or from 1.2 mA to 1.8 mA, or from 1.3 mA to 1.7 mA, or from 1.4 mA to 1.6 mA, or 1.5 mA. In embodiments, the electrode assemblies 200 described herein provide a maximum current density of less than 4 A/m$^2$, or of less than 3 A/m$^2$. In some embodiments, the electrode assemblies 200 described herein, including, e.g., the electrode interface 1 described herein, provide a maximum current density of from 1 A/m$^2$ to 3 A/m$^2$ to the subject 230. In some embodiments, the electrode assemblies 200 described herein, and particularly the electrode interface 1 described herein, provide a maximum current density of from 2.7 A/m$^2$ to 2.9 A/m$^2$, to the subject 230. In some embodiments, the electrode assemblies 200 described herein are used for performing closed loop transcranial direct current stimulation.

Embodiments of electrode assemblies 200 have been described in detail.

EXAMPLES

Example 1: Computer Modeling of Current Density of a Transcranial Direct Current Stimulation Electrode Assembly Having the Electrode Interface of FIG. 3A 1. Materials and Methods.

A CAD model was generated of a Transcranial Direct Current Stimulation Electrode Assembly having: (1) the electrode interface 1 of FIG. 3A; (2) an electrode 210 accommodated by the electrode interface 1; (3) a conductive contact medium having a conductivity of 4.0 S/m disposed in the conductivity passages 70 of the electrode interface 1 (SIGNAGEL®, Parker Labs, Fairfield, N.J.); and (4) a block (modeling human skin), wherein the contact surface 50 of the electrode interface 1 is placed on the block. Specifically, SimpleWare +CAD was used to load the Transcranial Direct Current Stimulation Electrode Assembly and to place the electrode 210 in the electrode interface 1 and the electrode interface 1 on the block. A Finite Element Method (i.e., FEM) model was generated using Simpleware ScanIP software.

Current modeling was done using COMSOL Multiphysics software, wherein manual parameters were inputted into the software for conductivities (i.e., S/m) of the electrode, conductive contact medium, and block. Specifically, conductivities of: (1) $6.545 \times 10^2$ S/m for the electrode; (2) 4 S/m for the SIGNAGEL®; (3) 0.45 S/m for the block (modeling human skin); and (4) $1e^{-15}$ S/m for the electrode interface 1 of FIG. 3A were inputted into the software. Additionally, the relative permittivity was set at 1, and a ground current was selected as the bottom side of the block modeling human skin. Inward current density was applied to the electrode-SIGNAGEL® interface, wherein inward current density= (input current (2 mA)/area of the electrode-SIGNAGEL® interface) and converted to $A/m^2$. The normal current density was then modeled by solving for the Laplace equation ($\nabla \cdot (\sigma \nabla V)=0$) for each set of conductivity values.

2. Results.

Figure 3E:
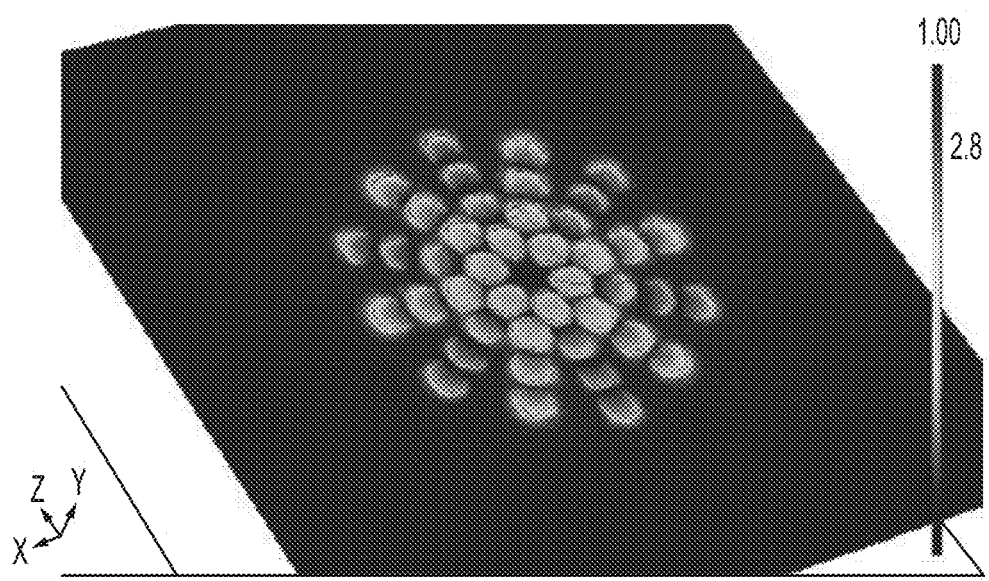
FIG. 3E is a representation of a computer model of current density of an electrode assembly having the electrode interface of FIG. 3A, with a scale of a standard electrode assembly and standard electrode interface identifying the current density of each different shade, wherein the scale is from 0 A/m$^2$ (bottom) to 3 A/m$^2$ (top)
Figure 3F:
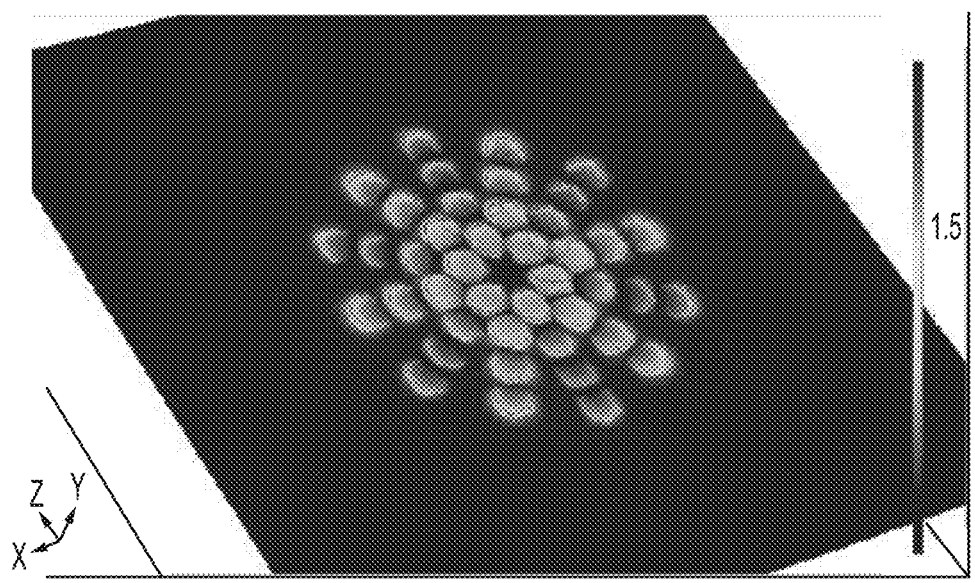
FIG. 3F is a representation of a computer model of current density of an electrode assembly having the electrode interface of FIG. 3A, with a scale adjusted to the electrode assembly having the electrode interface of FIG. 3A which identifies the current density of each different shade, wherein the scale is from 0 A/m² (bottom) to 2 A/m² (top)

As shown in FIGS. 3E-3F, computer models of current density were generated for the Transcranial Direct Current Stimulation Electrode Assembly having the electrode interface 1 of FIG. 3A. Such current density was scaled to a standard electrode interface and to the electrode interface of FIG. 3A. The standard electrode interface was the electrode interface described in U.S. Pub. No. 2016/0206871, such as, e.g., in FIG. 7 thereof. The computer model of current density generated in this example provided a maximum current density of 2.98 $A/m^2$.

Example 2: Computer Modeling of Current Density of a Transcranial Direct Current Stimulation Electrode Assembly Having the Electrode Interface of FIG. 4A 1. Materials and Methods.

A CAD model was generated of a Transcranial Direct Current Stimulation Electrode Assembly having: (1) the electrode interface 1 of FIG. 4A; (2) an electrode 210 accommodated by the electrode interface 1; (3) a conductive contact medium having a conductivity of 4.0 S/m disposed in the conductivity passages 70 of the electrode interface 1 (SIGNAGEL®, Parker Labs, Fairfield, N.J.); and (4) a block (modeling human skin), wherein the contact surface 50 of the electrode interface 1 is placed on the block. Specifically, SimpleWare+CAD was used to load the Transcranial Direct Current Stimulation Electrode Assembly and to place the electrode 210 in the electrode interface 1 and the electrode interface 1 on the block. A FEM model was generated using Simpleware ScanIP software.

Current modeling was done using COMSOL Multiphysics software, wherein manual parameters were inputted into the software for conductivities (i.e., S/m) of the electrode, conductive contact medium, and block. Specifically, conductivities of: (1) $6.545 \times 10^2$ S/m for the electrode; (2) 4 S/m for the SIGNAGEL®; (3) 0.45 S/m for the block (modeling human skin); and (4) $1e^{-15}$ S/m for the electrode interface 1 of FIG. 4A were inputted into the software. Additionally, the relative permittivity was set at 1, and a ground current was selected as the bottom side of the block modeling human skin. Inward current density was applied to the electrode-SIGNAGEL® interface, wherein inward current density= (input current (2 mA)/area of the electrode-SIGNAGEL® interface) and converted to $A/m^2$. The normal current density was then modeled by solving for the Laplace equation ($\nabla \cdot (\sigma \nabla V)=0$) for each set of conductivity values.

2. Results.

Figure 4E:
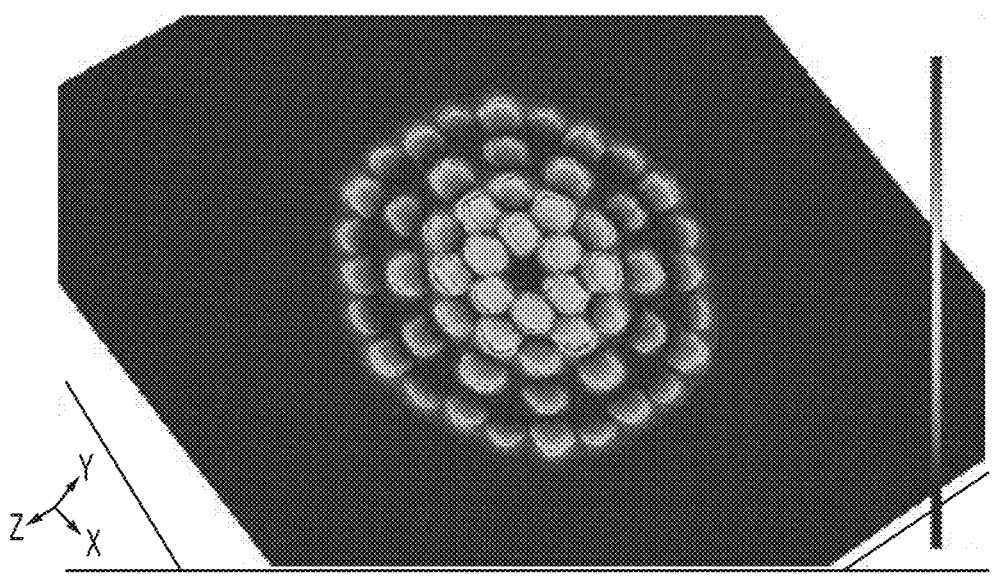
FIG. 4E is a representation of a computer model of current density of an electrode assembly having the electrode interface of FIG. 4A, with a scale of a standard electrode assembly and standard electrode interface identifying the current density of each different shade, wherein the scale is from 0 A/m² (bottom) to 3 A/m² (top)
Figure 4F:
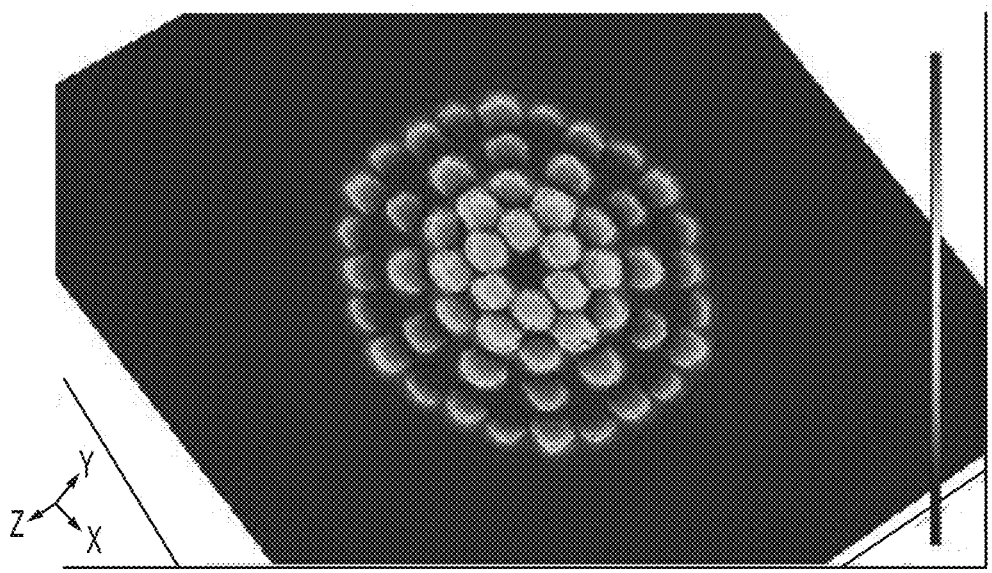
FIG. 4F is a representation of a computer model of current density of an electrode assembly having the electrode interface of FIG. 4A, with a scale adjusted to the electrode assembly having the electrode interface of FIG. 4A which identifies the current density of each different shade, wherein the scale is from 0 A/m² (bottom) to 3 A/m² (top)

As shown in FIGS. 4E-4F, computer models of current density were generated for the Transcranial Direct Current Stimulation Electrode Assembly having the electrode interface 1 of FIG. 4A. Such current density was scaled to a standard electrode interface and to the electrode interface of FIG. 4A. The standard electrode interface was the electrode interface described in U.S. Pub. No. 2016/0206871, such as, e.g., in FIG. 7 thereof, the contents of which are hereby incorporated by reference in their entirety. The computer model of current density generated in this example provided a maximum current density of 2.73 $A/m^2$.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., wherein X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

What is claimed is:

1. An electrode interface comprising:
  a body configured to be coupled to an electrode for delivery of electrical current therethrough, wherein the body comprises a non-contact surface and a contact surface opposing the non-contact surface, wherein the body defines a plurality of conductivity passages extending therethrough from the non-contact surface to the contact surface, and wherein each conductivity passage is disposed along a central axis and comprises:
    at least one branching inlet; and
    at least one branching subpassage extending from the at least one branching inlet to the contact surface, wherein each branching subpassage defines a plurality of branches, and wherein each branch diverges from the central axis and then extends to the contact surface.

2. The electrode interface of claim 1, wherein the body comprises a rim region and a recessed region for accommodating the electrode.

3. The electrode interface of claim 1, wherein the non-contact surface and the contact surface are parallel.

4. The electrode interface of claim 1, wherein each conductivity passage extends from a conductivity inlet defined by the body to a conductivity outlet defined by the body.

5. The electrode interface of claim 1, wherein the body defines at least six conductivity passages extending therethrough.

6. The electrode interface of claim 5, wherein the at least six conductivity passages are arranged in a hexagon configuration or a triangle configuration.

7. The electrode interface of claim 5, wherein the at least six conductivity passages are arranged in a hexagram configuration.

8. The electrode interface of claim 1, wherein each conductivity passage is tubular.

9. The electrode interface of claim 1, wherein the at least one branching subpassage defines at least two branches which diverge from the central axis and branch toward the contact surface.

10. The electrode interface of claim 1, wherein the at least one branching subpassage defines at least three branches which diverge from the central axis and branch toward the contact surface.

11. The electrode interface of claim 1, wherein each branch extends from the at least one branching inlet to a branching outlet defined by the body.

12. The electrode interface of claim 1, wherein:
  each conductivity passage includes a conductivity outlet defined by the body;
  each branching subpassage includes a plurality of branching outlets defined by the body, and
  the conductivity outlet of each conductivity passage and the respective branching outlets of each branching subpassage thereof are arranged in an inline configuration or a cross configuration.

13. An electrode assembly for performing transcranial direct current stimulation, the electrode assembly comprising:
  a neurostimulation device;
  at least two electrodes coupled to the neurostimulation device; and
  an electrode interface comprising a body coupled to each electrode for delivery of electrical current therethrough, wherein the body comprises a non-contact surface and a contact surface opposing the non-contact surface, wherein the body defines a plurality of conductivity passages extending therethrough from the non-contact surface to the contact surface, and wherein each conductivity passage is disposed along a central axis and comprises:
    at least one branching inlet; and
    at least one branching subpassage extending from the at least one branching inlet to the contact surface, wherein each branching subpassage defines a plurality of branches, and wherein each branch diverges from the central axis and then extends to the contact surface.

14. The electrode assembly of claim 13, wherein the at least two electrodes are ring electrode.

15. The electrode assembly of claim 13, further comprising a conductive contact medium disposed within the plurality of conductivity passages and the at least one branching subpassage.

* * * * *